(12) United States Patent
Kerr

(10) Patent No.: US 9,265,849 B2
(45) Date of Patent: Feb. 23, 2016

(54) SANITIZING APPARATUS

(71) Applicant: James Kerr, Old Orchard Beach, ME (US)

(72) Inventor: James Kerr, Old Orchard Beach, ME (US)

(*) Notice: Subject to any disclaimer, the term of this patent is extended or adjusted under 35 U.S.C. 154(b) by 0 days.

(21) Appl. No.: 14/149,787

(22) Filed: Jan. 7, 2014

(65) Prior Publication Data

US 2015/0190537 A1 Jul. 9, 2015

(51) Int. Cl.
*A61N 5/00* (2006.01)
*G01N 23/00* (2006.01)
*A61L 9/00* (2006.01)
*A61L 2/00* (2006.01)
*A62B 7/08* (2006.01)
*A61L 2/10* (2006.01)
*B08B 1/00* (2006.01)
*B08B 7/00* (2006.01)
*B08B 6/00* (2006.01)

(52) U.S. Cl.
CPC . *A61L 2/10* (2013.01); *B08B 1/002* (2013.01); *B08B 1/006* (2013.01); *B08B 7/0057* (2013.01); *B08B 6/00* (2013.01); *B08B 7/0028* (2013.01)

(58) Field of Classification Search
CPC ............ A61L 2/00; A61L 9/00; A61L 9/032; A61L 9/122; A61L 9/20
USPC ......... 422/5, 24, 124, 307; 250/455.11, 492.1
See application file for complete search history.

(56) References Cited

U.S. PATENT DOCUMENTS 3,667,134 A * 6/1972 Rockson ........................... 34/60

* cited by examiner

*Primary Examiner* — Monzer R Chorbaji
(74) *Attorney, Agent, or Firm* — James G. Shelnut; JEDA Patentry

(57) ABSTRACT

The present disclosure presents sanitization devices and methods. More particularly, the disclosure presents devices and methods that significantly reduce or eliminate the activity of germs, bacteria and/or other infectious microorganisms from objects such as TV remotes, cell phones, electronic devices and personal and other handheld devices. The devices and methods use a pre-cleaning component to substantially remove radiation blocking debris allowing the germicidal radiation to exposes areas of the object that would not be exposed if the debris had not been removed allowing for improved sanitization.

24 Claims, 5 Drawing Sheets

SANITIZING APPARATUS

FIELD OF DISCLOSURE

The present disclosure relates to sanitization devices and methods. More particularly, the disclosure relates to devices and methods that significantly reduce or eliminate the activity of germs, bacteria and/or other infectious microorganisms from objects such as TV remotes, cell phones, electronic devices and personal and other handheld devices. The device and method uses a pre-cleaning component to substantially remove radiation blocking debris allowing the germicidal radiation to exposes areas of the object that would not be exposed if the debris had not been removed.

BACKGROUND OF THE DISCLOSURE

The surfaces of many objects used in everyday life tend to attract and harbor potentially harmful infectious organisms, such as microbes, pathogens, viruses, bacteria and the like. Particularly infected are objects that are passed from one person to another without the benefit of cleaning or sanitizing. Objects that are handled or breathed-on by different people, or come in contact with surfaces contaminated by other people or animals, can themselves become contaminated. If these objects then contact another person, they can transmit diseases. Even the hands and clothing of medical or healthcare personnel can serve to transmit diseases. This contamination problem is particularly acute with objects used continually by different people. If they are not sterilized between the different users of the objects they can serve as the vector to transmit the disease from one person to the next. Examples include TV remotes in hotel rooms and medical devices.

One method of reducing the impact of infectious organisms are exposure to germicidal ultraviolet bulbs. The bulbs are generally short wave low pressure mercury vapor tubes that produces ultraviolet wavelengths that are lethal to microorganisms. Approximately 95% of the ultraviolet energy emitted by these bulbs is at and around the mercury resonance line of 254 nanometers. This wavelength is in the region of maximum germicidal effectiveness and is highly lethal to virus, bacteria and mold spores. It deactivates the DNA of bacteria, viruses and other pathogens and thus destroys their ability to multiply and cause disease. Specifically, UV-C light causes damage to the nucleic acid of microorganisms by making them form covalent bonds between certain adjacent bases in the DNA. The formation of such bonds prevents the DNA from being unzipped for replication, and the organism is unable to reproduce. In fact, when the organism tries to replicate, it dies. UVC radiation has extremely low penetrating ability and does not penetrate past the dead-cell layers of the skin. UV will cause eye irritations or burns after prolonged exposure.

Devices for sanitizing objects that might have harmful infectious organisms on their surfaces have been described, for example, U.S. Pat. Application 2005/0063922A1 to Wesley et al. The devices use sanitizing bulbs that emit sanitizing radiation and shine that radiation onto the surfaces of the object to be sanitized. The sanitizing radiation is a light-of-sight process in which the radiation impinges directly onto the surfaces which are in an unimpeded straight line from the source to the surface. As such, anything in the way of the direct line from the irradiation source to the surface, such as dirt particles and the like on the surface, will prevent those covered surface areas from being sanitized. This is a recognized problem with the devices currently available. One method to improve the problem, in one case, is by rotating the object to be sanitized so that more surface can be aligned in a line-of-line configuration with the radiation source as the device rotates. Another method to improve this problem is by providing mirrors and/or mirrored surfaces that reflect the sanitizing radiation at different angles to the surface areas to be sanitized. One drawback to mirrors is that the intensity of the sanitization radiation is reduced the further it has to travel, in inverse proportion to the distance, such that as the radiation gets reflected around the chamber the distance the radiation travels increases and the intensity of the radiation decreases. Thus any sanitization that depends on reflected sanitization radiation will require a longer radiation time to be effective as a sanitization device and/or process. Although the prior art addresses this problem, they are only a work-around from the cause of the problem. None of the solutions described in the prior art remove the radiation blocking material.

SUMMARY OF THE EXEMPLARY EMBODIMENTS

It is an object of the current invention to overcome the deficiencies commonly associated with the prior art as discussed above and provide devices and methods that eliminate or significantly reduce the activity of infectious microorganisms from objects after substantial removal of surface debris.

In a first embodiment, disclosed and claimed herein is an apparatus for sanitizing an object including a compartment having a top portion, a bottom portion and side portions and configured to envelop the object to be sanitized; an ingress positioned in the compartment; a component for reducing debris from the surface of the object to be sanitized; and at least one radiation source within the compartment, wherein the at least one radiation source can provide UV radiation for deactivating infectious organisms.

In a second embodiment, disclosed and claimed herein is the above embodiment wherein the UV radiation is at least 253.7 nm.

In a third embodiment, disclosed and claimed herein are the above embodiments wherein the component for reducing debris is at least one of a brush mechanism, an adhesive mechanism, an air impingement mechanism, a wiping mechanism or an electrostatic mechanism.

In a fourth embodiment, disclosed and claimed herein are the above embodiments, wherein the component for reducing debris is positioned proximal to the ingress.

In a fifth embodiment, disclosed and claimed herein are the above embodiments wherein the apparatus is a configuration that contains all or essentially all of the UV radiation from the radiation source from leaking out of the device when in use.

In a sixth embodiment, disclosed and claimed herein are the above embodiments wherein the ingress comprises an aperture through which the object can be, wherein the ingress may be a cradle into which the object can be placed, the cradle movably attached to the compartment and capable of moving into the compartment through the aperture.

In a seventh embodiment, disclosed and claimed herein are the above embodiments containing a spring loaded platform positioned proximal to the ingress and movable between positions, wherein the object to be sanitized can be placed through the ingress to push the platform to a position distal to the ingress into a locked, releasable position by a releasable latch which can release when a desired sanitizing cycle ends, wherein the object is enveloped by the compartment when the platform is pushed into the locked position.

In an eighth embodiment, disclosed and claimed herein are the above embodiments wherein a top portion of the compartment is attached to at least one side portion of the compartment by a hinging mechanism and is capable of covering the ingress, wherein the top portion can be swung away from the compartment, an object placed inside the compartment and the top portion swung back into its original position, enveloping the object.

In a ninth embodiment, disclosed and claimed herein are the above embodiments containing a signaling component for signaling when the radiation source is emitting radiation and when it is not and electronic connections for charging devices, connecting electronic devices, communication devices, internet devices, and combinations thereof.

In a tenth embodiment, disclosed and claimed herein are the above embodiment, wherein the compartment is sized to accept cell phones and TV remotes, other handheld devices, smart pads, keypads, jewelry, keys, credit cards, money, toiletry items, food related items including food items that come into contact with food, such as trays, dental and medical equipment and devices, writing utensils, kitchen utensils, books, magazines, gaming items like dice and playing cards, toys, balls, personal hygiene items, such as combs, brushes, toothbrushes, baby related objects like rubber nipples, containers, cordless telephone, smart phones, wireless headsets, portable media devices, digital cameras, video recorders, audio recorders, portable gaming devices, portable computing devices, tablet computers, laptop computers, notebook computers, electronic reading devices, personal digital assistants (PDA), palmtop computers, handheld computers, pen computers, ultra-mobile personal computers, pagers, portable navigation devices, personal navigation assistants, for example, portable Global Positioning System units, personal electronic devices, toys, balls, personal hygiene devices, devices used by infants, containers, portable data devices, gaming items, toiletry items, food items, dental and medical instruments, writing utensils, kitchen utensils, books, magazines, and other objects which can carry infectious organisms.

In other embodiments of the current disclosure are methods of sanitizing an object, including the steps of providing one of the apparatuses of the above embodiments, positioning the object to be sanitized through the ingress into the compartment; removing a portion of the debris from the surface of the object; irradiating the object with radiation from the one or more radiation source, and removing the object from the apparatus.

DETAILED DESCRIPTION OF THE DISCLOSURE

Figure 1:
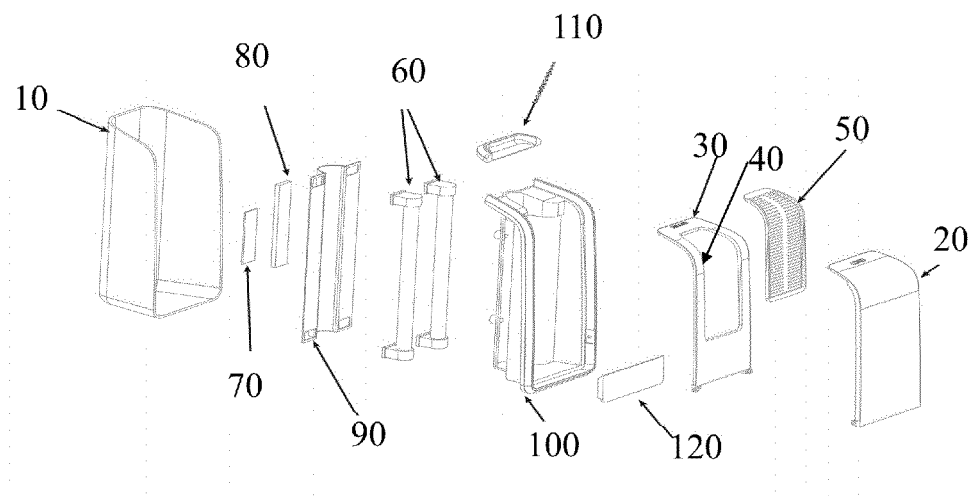
FIG. 1 is an exploded illustration of one embodiment of the current disclosure in which an object to be sanitized is placed into a compartment 40 for sanitization through brushes 50 to remove debris.

The term "compartment" as used herein means the enclosure into which a device for sanitization is placed and wherein sanitization is to take place. The compartment may be configured to enclose small hand-held devices as well as larger devices, such as a television, furniture, sports equipment and the like.

The term "apparatus" is used herein to include the compartment and any other peripheral components.

As used herein the term "envelope" means to completely surround and enclose.

As used herein the term sanitized refers to a reduction of the activity of infection organisms and is not meant to infer 100% elimination of all infectious organisms.

As used herein the term "deactivate" means that the infectious organism is rendered non-infectious, which includes the killing of the organisms.

Disclosed and claimed herein is an apparatus for sanitizing an object, such as, for example, the surface of an object, including a compartment having a top portion, a bottom portion and side portions and configured to envelop the object to be sanitized; an ingress positioned in the compartment; a component for reducing debris from the surface of the object to be sanitized; and at least one radiation source within the compartment, wherein the at least one radiation source can provide UV radiation for deactivating infectious organisms.

The apparatus may be constructed from any of a number suitable materials, such as, for example, lightweight, rigid plastic, plastic composite, thermoplastic, radiation cured materials, metal, or a combination. Suitable plastics include polyvinyl chloride, polypropylene, polyolefin, acrylonitrile-butadiene-styrene, polyethylene, polyurethane, polycarbonate, high-impact polystyrene, nylon or blends thereof. The apparatus may be constructed so that the compartment completely encloses an object to be sanitized when in use. Likewise the compartment may be constructed so that only a portion of the object to be sanitized is enclosed thereby allowing partial sanitization of the object as desired. The apparatus and compartment may take on any of a number of shapes or styles chosen for its utility, style, or eye-appeal. For example the apparatus and compartment may be higher than it is wide or vice versa. The sidewalls could be vertical or could be slanted in or out depending on the desired design of the device. The overall shape may be square, rectangular, triangular, oval, cylindrical, essentially spherical with a flat stabilizing bottom, or other appealing polygonal shape. The apparatus may also include a stabilizing base such that the apparatus is stabilized to falling over.

The ingress may be positioned anywhere desirable in the compartment of the apparatus depending on the method used for placing the object to be sanitized into the compartment, such as through the top, the sides, the bottom or a combination. The ingress is configured to allow the object to be sanitized to be placed into the compartment. A mechanism to enclose the compartment is also present which, in operation, will cover the ingress and not allow any substantial amount of sanitizing radiation to be emitted. This can be a hinged cover, a removable cover, a cap, a sliding cover, or other mechanism known in the art to cover an opening.

The ingress may be designed so that the object to be sanitized may be placed by hand into the compartment of the apparatus. This may be through the top, the side or a combination of both. Other mechanisms may also be present, such as, for example, a bracket that removably attaches to the object, wherein the bracket and object may be placed by hand into the compartment. In other embodiments, the apparatus may contain a cradle into which the object to be sanitized may be placed; and the cradle may be capable of sliding in and out of the compartment either as a unit or by a pivoting mechanism attached to the apparatus through any of the surfaces of the apparatus, such as the side.

In another embodiment, the ingress may result from a "clam-shell" type opening in which the top and a portion of all sides of the apparatus are capable of being opened to allow the object to be sanitized to be placed into the compartment and the clam-shell closed over the object.

In another embodiment, the top portion of the compartment is attached to at least one side portion of the compartment by a hinging mechanism and is capable of covering the ingress, wherein the top portion is capable of being swung away from the compartment to allow the object to be positioned in the compartment and returning to its original position to envelop the object.

The compartment contains one or more one or more bulbs which emit radiation that deactivates infectious organisms. The radiation includes, for example, UV radiation, UVC radiation and other wavelengths that deactivate infectious organisms, including radiation emitted at a wavelength around 254 nm. The current disclosure is not limited to only bulbs, but includes other devices which emit sanitizing radiation, such as, for example LED devices.

The most effective wavelength for killing or inactivating microorganisms is the 100-290 nm range, which is the UVC wavelength band. It is composed of short wavelengths from 200 to 280 nm. Most commercially available UVC bulbs are low pressure mercury vapor bulbs that give off a wavelength of 254 nm, which is near the optimum for killing or inactivating microorganisms. Low-pressure mercury-vapor bulbs usually are made with a quartz bulb in order to allow the transmission of short wavelength light. Natural quartz allows the 254 nm wavelength to pass through but blocks the 184 nm wavelength. Synthetic quartz may also be used which allows the 184 nm wavelength to pass, however 184 nm can produce ozone. The bulbs are generally doped with materials that suppress or eliminate the 184 nm wavelengths in low-pressure mercury vapor bulbs.

Not to be held to theory, a wavelength of 254 nm UV will break down the molecular bonds within the DNA of microorganisms producing thymine dimers in their DNA thereby destroying them, rendering them harmless or prohibiting growth and reproduction. It is a process similar to the UV effect of longer wavelengths UVB on humans. However UVB and UVA do not act as sanitizing radiations.

As an example, commercially available T5 size UVC germicidal bulbs range in input power from about 7-16 watts for a tube which is 11.3 inches long. Output wattage for these bulbs, consisting primarily of 254 nm emissions, is approximately 2-4 watts with an efficiency rating of between about 20 and about 40 $\mu W/cm^2$ at a distance of 1 meter from the tube. Power intensity of approximately 1400 to 2800 $\mu W/cm^2$ measured at a distance of 2 inches from the bulb surface is achieved.

Again not to be held to theory, it has been reported that to reach a 99% kill rate of *bacillus anthracis* a dosage of 8,700 $\mu W$ second/$cm^2$ is required. Thus, in the current example and using the equation: Intensity×Exposure Time=$\mu W$ second/$cm^2$, a bulb with a minimum power intensity of 1400 $\mu/cm^2$ at 2 inches from the bulb surface, an exposure time of less than 7 seconds is required. Of course a longer time will improve the kill rate for *bacillus anthracis*. Other notable 99% kill rate exposure requirements for UVC (measured in $\mu W/cm^2$) are: *E-coli*=6500, *Salmonella typhosa*=6000, Dysentery=4200 and *Cholera*=6500. It should be noted that in the example a 7 second exposure would be sufficient to provide a 99% kill rate of all the aforementioned bacteria. Viruses are also killed by UVC, some of the toughest being poliovirus and rotavirus, which require 21,000 $\mu W/cm^2$ for a 99% kill rate. Thus using the bulbs of the above example, a 15 second exposure would provide a 99% kill rate. Also molds and yeasts can be killed by UVC exposure. Other UV wavelengths are known to deactivate certain infectious organisms and are included here in the current disclosure.

Sanitizing bulbs may be chosen for their specific radiation output. For example, bulbs may put out both about 184 nm light as well as light around 254 nm. In this case there may be an amount of ozone generated, which can be helpful in sanitization, but can be considered toxic. Or the bulbs can be chosen to only put out about 254 nm radiation. If there is ozone generated by the bulbs, an ozone absorbing material may be present as a part of the compartment or the apparatus which substantially absorbs the ozone to a safe level before it can be released into the general atmosphere.

The sanitizing radiation is a line-of-sight process in which the radiation impinges directly onto the surfaces of objects. The line-of-light may be an unimpeded straight line directly from the source to the surface. The line-of-sight includes configurations wherein the sanitizing radiation is reflected from mirrors or other reflecting surfaces, which direct the sanitizing radiation onto surfaces which may not be in the direct line from the radiation source to the surface, thus allowing an increase in the amount of surface that can be sanitized during the sanitation process. As such, anything in the way of the direct line from the irradiation source to the surface, such as dirt particles and the like on the surface, will prevent those covered surface areas from being sanitized. As mention, this is a recognized issue and has been improved, in one case, by rotating the object to be sanitized so that more surface can be aligned in a line-of-line configuration with the radiation source. Also, as mentioned, this problem has been further improved by providing mirrors and/or mirrored surfaces that reflect the sanitizing radiation at different angles to areas, again in a line-of-sight configuration, that would not be accessible in a straight line-of-sight configuration. As stated the intensity of the sanitization is reduced the further it has to travel, in inverse ratio of the square of the distance, such that as the radiation gets reflected around the chamber the distance the radiation travels increases and the intensity of the radiation decreases. Thus any sanitization that depends on reflected sanitization radiation will require a longer radiation time to be effective as a sanitization device and/or process. Reflective radiation, in the current disclosure, is complimentary to the main line-of-sight radiation.

The current disclosure provides for a component for reducing debris that resides on the surface of the object to be sanitized so that, when in use, the radiation may reach those areas on the surface of the object to deactivate infectious organisms which would not have been exposed if the debris had not been removed. In some embodiments, the component for reducing debris may be positioned proximal to the ingress either after the ingress such that debris reducing component is inside the compartment, or before the ingress, such that the debris reducing component is outside the compartment. In either configuration the object to be sanitized is placed through the debris reducing component prior to being exposed to sanitizing radiation. In other embodiments of the current disclosure the object to be sanitized may experience one or more of the debris removing components when placed into the compartment of the apparatus.

The component for reducing debris may be a brush mechanism wherein the mechanism may be positioned at the ingress, either in front of or behind the ingress, through which the object to be sanitized is placed. The brushes may be made of any of a number of suitable material, such as, for example, nylon, polyester, or other materials known in the art. As the object moves through the ingress the brush or brushes contact the surface of the object and remove a substantial amount of debris. In operation the object, which now has a reduced amount of debris on its surface, can be irradiated with sanitizing radiation more effectively than if the brushes were not present.

After sanitization the object may be removed from the component without passing through debris-reducing component or the object may pass back through the brush mechanism. In the former case the brushing mechanism may lift out of the way when a door, or cover, is lifted to allow access to the object. This may be done with an automatic clipping mechanism that engages when the door, or cover, is closed such that when the door, or cover, is opened the brushing mechanism stays removable attached to the door, or cover. When the device is removed and door or cover is replaced, the brushing mechanism is disengaged from the door, or cover, ready for the next object to be placed through it. In other embodiments, after sanitization, the object passes back through the brushing mechanism when being removed which may or may not redeposit some of the original debris. The removal of debris is primarily to allow the sanitizing radiation to impinge on the surface areas under the debris, although removal of debris serves other purposes such as cleanliness. In other embodiments the compartment may include an egress through which the now radiation sanitized object can pass through as it removed from the apparatus without going through the brush mechanism.

In other embodiments the component for removing debris may be one or more rollers having a surface onto which debris may be attracted, such as, for example, a tacky surface or an electrostatic surface. When the object to be sanitized is placed through the one or more rollers the debris gets picked up onto the surfaces of the roller thus exposing more surface area on the object to receive sanitizing radiation. The rollers may be removed, cleaned and replaced during routine maintenance to remove the accumulated debris that has been removed, or there may be a removal surface layer to which the debris has attached which can then be peeled off and replaced with a new layer. Additionally, there may be a number of layers of debris attaching material which, when the first, debris loaded layer is removed, the layer behind it to is now exposed and can be used to attach debris, such as, for example, a roll of adhesive tape with adhesive layer directed outwardly.

In other embodiments the component for removing debris may be an air impingement device wherein air is directed across one or more surfaces of the object to be sanitized. The air may impinge at the ingress and be applied as the object is being placed into the compartment. Alternatively the object may be placed into the compartment and air then is impinged onto one or more of the object's surfaces. At this stage the compartment may be open or closed.

The component for reducing debris may be a wiping mechanism wherein the component is attached to the compartment or apparatus and contains wipes. The wipes can be used by the user to physically wipe the surfaces of the object to be sanitized to reduce debris on the object's surface, prior to placing the object into the apparatus through the ingress for sanitization. The wipes may be comprised of, for example, cloth, paper, plastic or other material which can be used to wipe a surface. The wipes may be comprised of, for example, liquids, pastes and electrostatic capabilities which can aid in debris removal. The wipes further may be comprised of antibacterial ingredients which may aid in the sanitization of the object, including sodium hypochlorite and metal ions, such as, for example, silver, copper or zinc ions.

The compartment may include a support on which the object to be sanitized rests when in use, which may be the bottom of the compartment or a bracket for holding the object up-right or in other desired positions. It can be made from the same material as the apparatus or a different material. One or more of the interior surfaces of the compartment may be comprised of reflective materials chosen to reflect the sanitizing radiation, thus aiding in allowing the sanitizing radiation to reach additional portions of the object surfaces to be sanitized. The support into or onto which the object is placed may be rotatable during operation.

The object to be sanitized may be removed by a spring loaded device positioned within the compartment proximal to the ingress. The object to be sanitized can be placed through the ingress onto the spring loaded device and pushed inward to a position distal to the ingress into a locked, releasable position. For example, a toaster-type mechanism may be used as the spring loaded device which utilizes an electromagnet to lock the device and object in place in the compartment during sanitization. After the sanitization process is complete, as determined by the radiometric sensor and the logic device, the electromagnet turns off and the spring engages to "pop-up" the device though the original ingress. Of course other mechanisms known in the art can be used to eject the object when sanitization is complete.

In further embodiments, the object to be sanitized may be a pass-through system in which the object is continuously conveyed through the compartment by such devices as a conveyor belt, or rollers or other transporting mechanisms. The debris removing component may be brushes, tacky rollers, air impingement and the like.

The apparatus and/or compartment are designed so that all or essentially all of the sanitizing radiation is prevented from escaping the compartment. Other, non-sanitizing radiation, such as visible light, may be allowed to escape such as, though a window through which the object to be sanitized can be seen. The window may be made of any material which blocks, or absorbs, UV radiation while allowing harmless visible to pass through, such as, for example, soda-lime glass, Plexiglas, polyester plastic, high impact polystyrene and the like.

The apparatus includes a radiometer sensor which senses the amount of radiation that the sanitizing bulbs have emitted. The sensor is electrically connected to a logic device which determines the required amount of sanitizing radiation to be emitted from the sanitizing bulbs. The logic device may be programmed for specific infectious organisms or programmed for general sanitization as desired, including, for example, time of sanitization, amount of energy, and the like. In the case of a conveying device, the logic device determines the speed with which the object is conveyed through the compartment. The logic device may be capable of reprogramming as desired.

The apparatus may contain a switching device with activates the sanitization process when the door or cover completely encloses the compartment so that essentially no radiation is allowed to emit from the apparatus. If the door or cover should prematurely open the switching device can turn the sanitization bulbs off.

The apparatus may also contain a signaling device which notifies the user when the sanitization process has completed and the object may be removed from the compartment. These devices include, for example, one or more lights, color-changing tabs, audio signals or combination.

The signaling component may also take the form of a window in the top or side of the apparatus through which only visible light from the radiation source can be seen when the radiation source is emitting radiation. The window is comprised is of material that is absorbent to harmful radiation such as UV radiation. In this manner a user can observe when the radiation source is emitting sanitizing radiation and when it has completed its operation and it is safe for the user to remove the object through an ingress, egress or other method.

While not to be restricted, the apparatus may contain any number of additional components, such as, for example, an anchoring mechanism for anchoring the apparatus to a table, a bench or other solid object to prevent unauthorized removal.

Objects suitable for sanitization using the apparatuses and methods disclosed herein may range from cell phones and TV remotes, to other handheld devices, smart pads, laptops, keypads, jewelry, keys, credit cards, money, toiletry items, food related items including food items that come into contact with food, such as trays, dental and medical equipment and devices, writing utensils, kitchen utensils, books, magazines, gaming items like dice and paying cards, toys, balls, persona hygiene items, such as combs, brushes, toothbrushes, baby related objects like rubber nipples, containers, and other objects which can carry infectious organisms from one person to another. The apparatus may be configured to enclose large objects such as shopping carts, bicycles, large machinery, arcade video games and other large objects which can carry infectious organisms from one person to another.

Drawing attention to FIG. 1, an exploded illustration of one embodiment of the current disclosure is shown. Here the object to be sanitized is placed into the compartment of the apparatus passing through and ingress which contains debris removing brushes. A lid is closed to completely envelope the object and UVC radiation sources are turned on to reduce or eliminate the activity of any infectious materials present. The UVC sources then turn off after the cycle is completed, the lid disengaged and the object removed. The apparatus is defined by the main housing 10, in this case including the bottom and three sides of a compartment, and 20, the outer lid defining the fourth side and top of a compartment. An inner lid 30 positioned under the outer lid contains an ingress 40. A debris removal component 50, in this case a brushing mechanism, is positioned at the ingress, 40. Positioned inside the compartment are two radiation sources, here UVC emitting lamps 60. Further positioned in the compartment is a PCB 70, a ballast 80, a lamp bracket 90 and a reflector unit 100. An upper cover 110 and a lower cover 120 are also shown.

Figure 2:
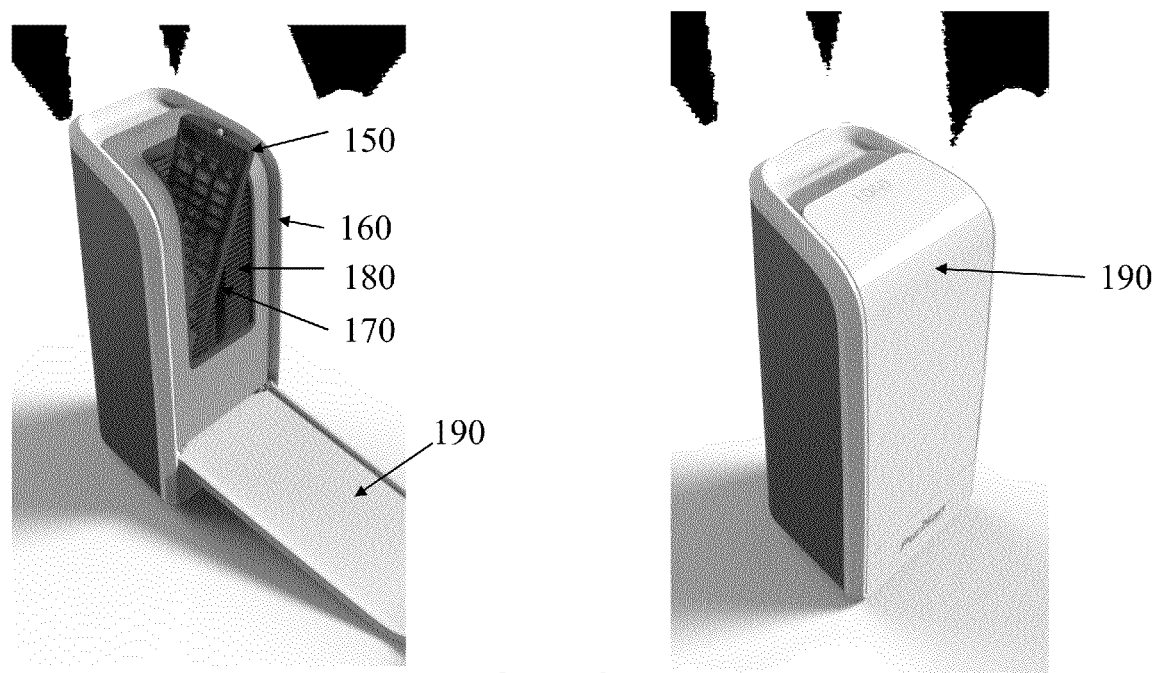
FIG. 2 is an illustration of the apparatus in FIG. 1 in operation.

FIG. 2 shows the apparatus of FIG. 1 in operation. The object to be sanitized 150 is placed into the compartment of the apparatus 160 through the ingress 170. At the ingress is positioned debris removing brushes 180 through which the object passes. The outer lid 190 is then closed completely enveloping the object and sanitization begins. When the sanitization is complete, the radiation sources stop irradiating, the lid disengages from the apparatus and the object is removed, not shown.

Figure 3:
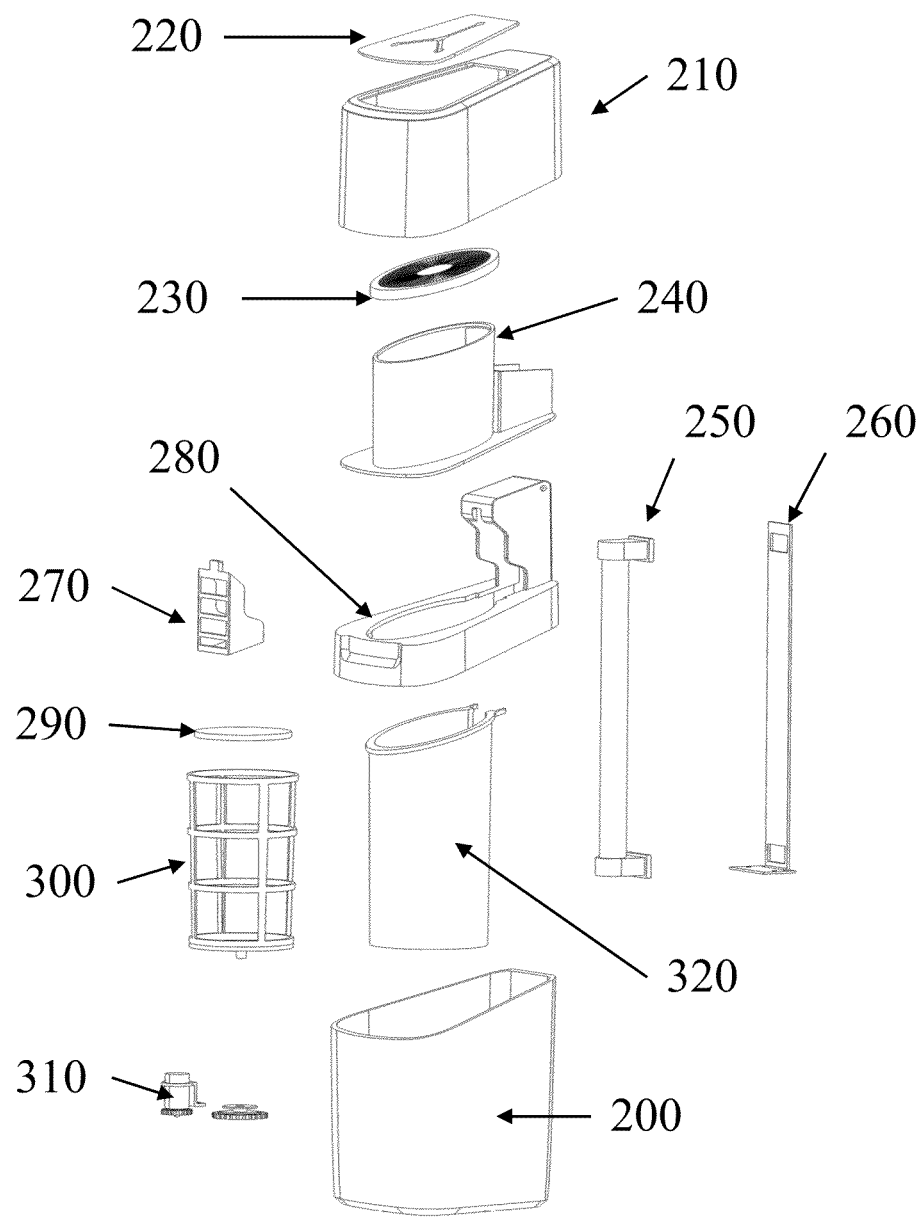
FIG. 3 is an exploded illustration of another embodiment of the current disclosure in which an object to be sanitized is placed into a compartment for sanitization through brushes 230 to remove debris and the object rotates.

FIG. 3 is an exploded illustration of another embodiment of the current disclosure. In this case the object to be sanitized is placed into the compartment of the apparatus through an ingress, followed by debris removing brushes. The object then proceeds to, and is held in, a basket. The UVC radiation sources are turned on and the basket rotates within the compartment. The UVC sources then turn off after the cycle is completed, the lid is disengaged and the object removed. The apparatus is defined by a lower housing 200, and an upper housing 210, which contains an ingress 220 creating a compartment. Below the ingress are debris removing brushes 230 which are attached to an inner lid 240. A UVC radiation source 250 is position in the compartment in a lamp bracket 260 and contains a bulb cover 270. A basket 300 and a basket insert 290 are positioned in a bucket 320 in the compartment capable of receiving an object to be sanitized. A motor 310 for rotating the basket 300 and an object positioned therein is position at the bottom of the lower housing 200. A mid housing 280 is positioned between the upper housing 210 and the lower housing 200.

Figure 4:
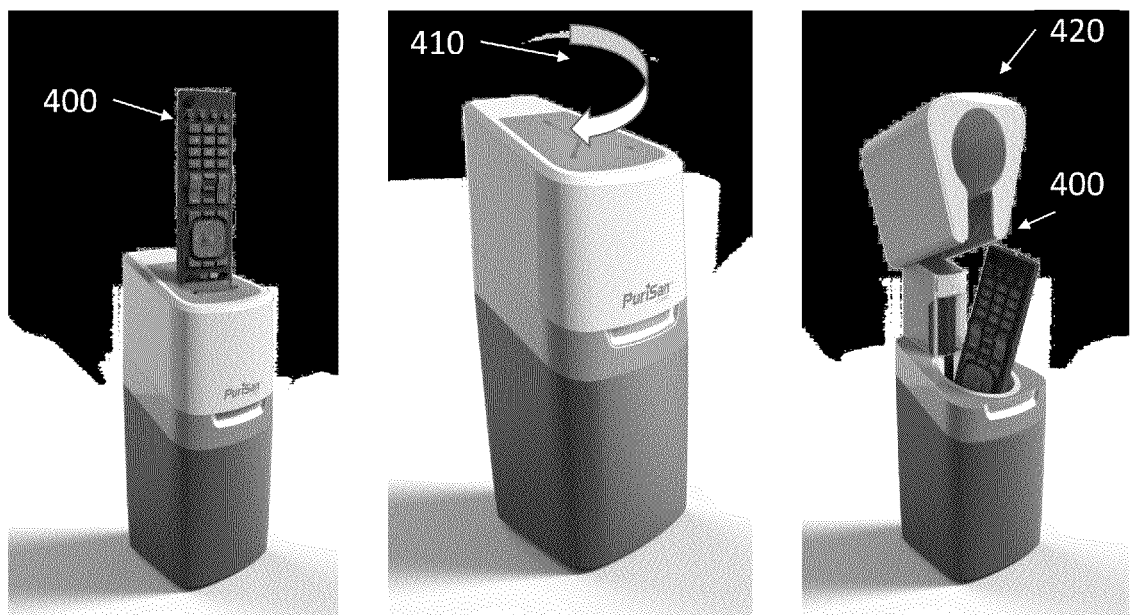
FIG. 4 is an illustration of the apparatus in FIG. 3 in operation.

FIG. 4 shows the apparatus of FIG. 3 in operation. The object to be sanitized 400 is placed into the ingress 220 in the upper housing. Object proceeds through the brushes and is positioned in the basket, not shown. The basket rotates in either direction 410 as the UVC radiation source is turned on and The UVC radiation sources are turned on and the basket rotates within the compartment. The UVC sources then turn off after the cycle is completed, the lid is disengaged 420 and the object 400 removed.

Figure 5:
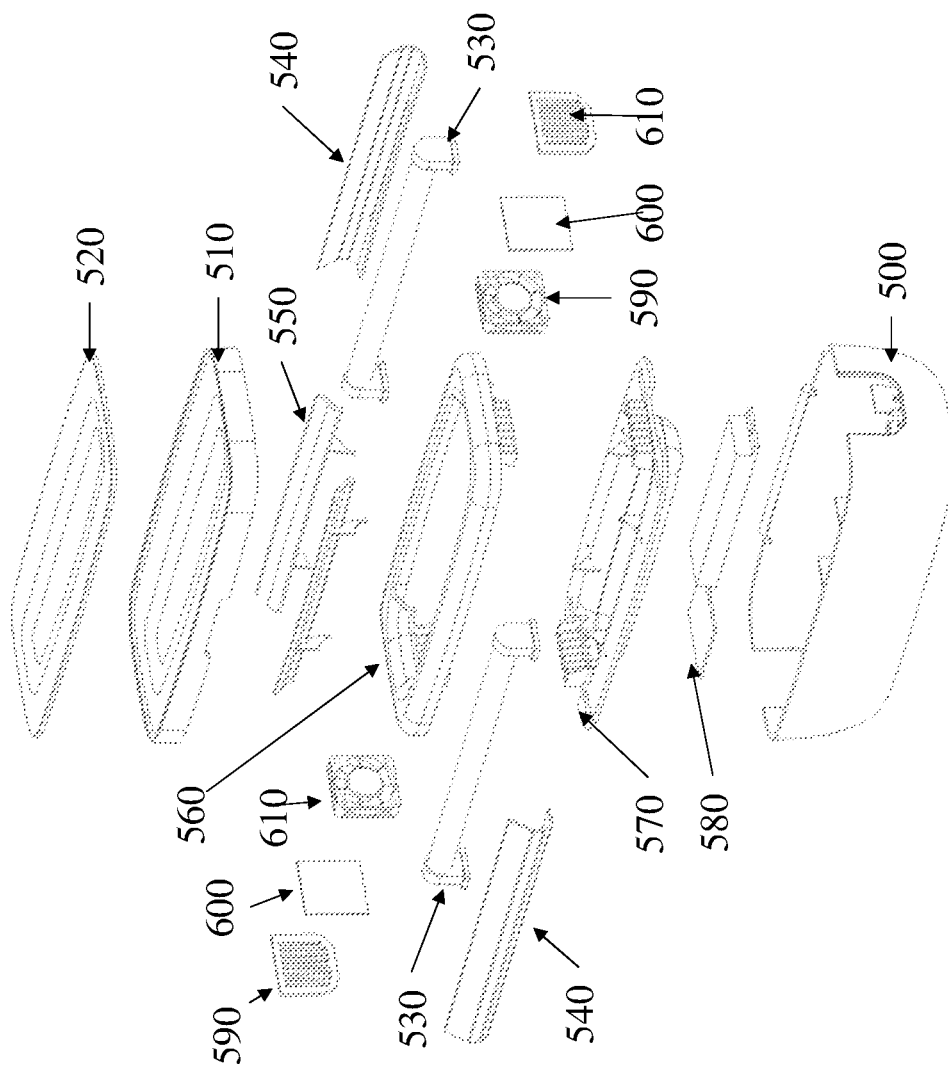
FIG. 5 is an exploded illustration of another embodiment of the current disclosure in which an object to be sanitized is placed into a compartment for sanitization and air impinges on the object to remove debris using fans 590.

FIG. 5 is an exploded illustration of a further embodiment of the current disclosure. In this embodiments the apparatus contains a "clam-shell" lid which lifts up by way hinges. The object to be sanitized is placed inside the compartment of the apparatus. Air is then impinged on the surfaces and recesses of the object to remove debris by way of fans, arranged to draw air into and out of the compartment. Filters are present to remove any particles coming into the compartment and from leaving the compartment. The UVC radiation sources are turned on either during or after the fans have impinges the object. The UVC sources then turn off after the cycle is completed, the lid is disengaged and the object removed. The apparatus is defined by a main housing 500 and a main lid 510. The lid has a lid insert 520 for holding an object which has been sanitized. Inside the compartment are positioned UVC radiation sources 530 connected to a ballast 580 and includes lamp reflectors 540, and lamp covers 550. An upper cage 560 and a lower cage 570 are positioned inside the compartment for structural and positional purposes. Fans for removing debris 590 are positioned in the compartment with associated particle filters 600 and vents 610.

Figure 6:
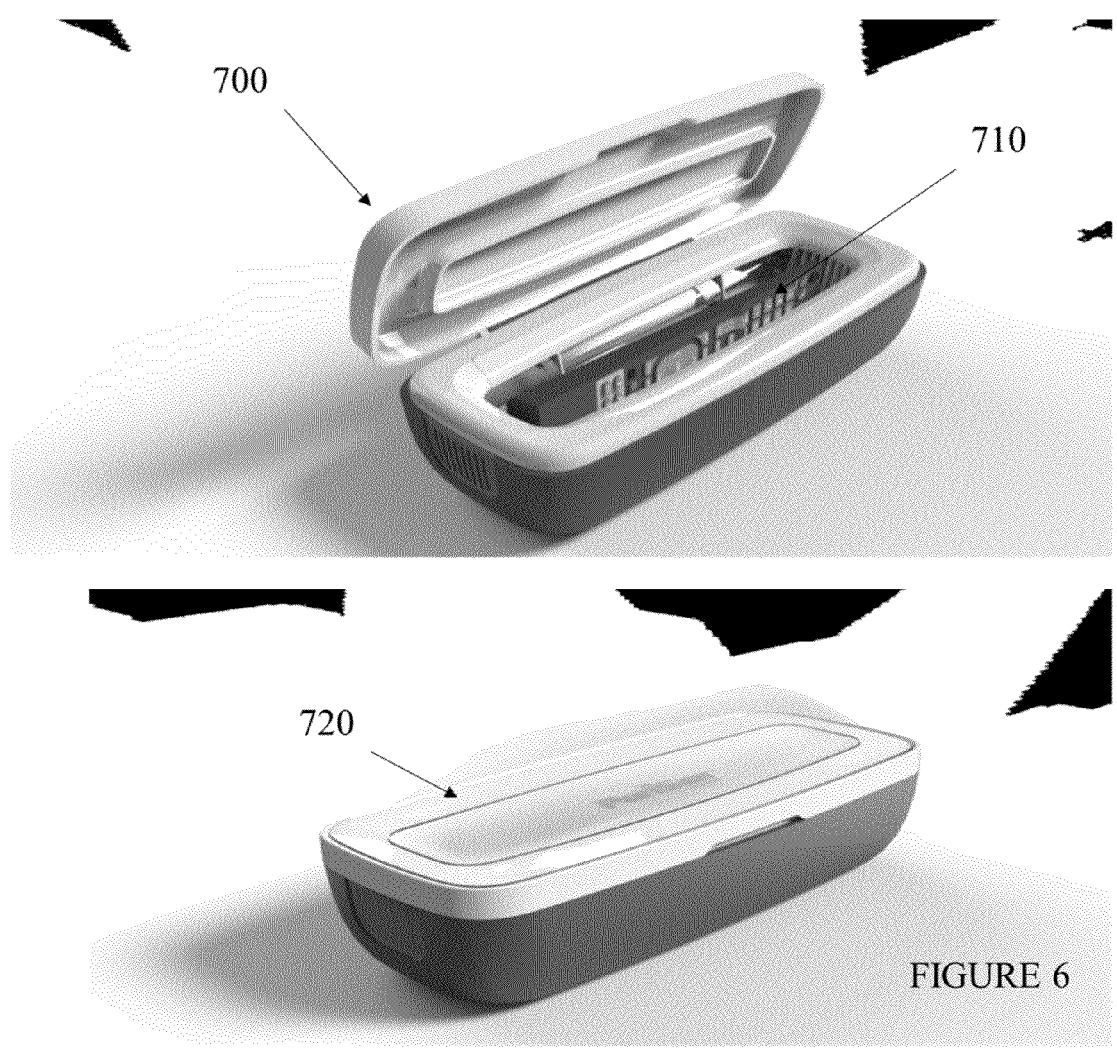
FIG. 6 is an illustration of the apparatus in FIG. 5 in operation.

FIG. 6 shows the apparatus of FIG. 5 in operation. The lid 700 is lifted and the object to be sanitized 710 is placed inside. The lid is closed 720 and the fans are started and the UVC radiation sources are turned on, not shown. The UVC sources and fans then turn off after the cycle is completed, the lid is disengaged and the object removed.

I claim:

1. A apparatus for sanitizing an object, comprising:
   a. a compartment comprising a top portion, a bottom portion and side portions and configured to envelop the object to be sanitized:
   b. an ingress positioned in the compartment;
   c. a component for reducing debris from the surface of the object to be sanitized; and
   d. at least one radiation source within the compartment; wherein the at least one radiation source can provide UV radiation for deactivating infectious organisms.

2. The apparatus of claim 1, wherein the UV radiation is at least 253.7 nm.

3. The apparatus of claim 1, wherein the component for reducing debris is at least one of a brush mechanism, an adhesive mechanism, an air impingement mechanism, a wiping mechanism or an electrostatic mechanism.

4. The apparatus of claim 1, wherein the component for reducing debris is positioned proximal to the ingress.

5. The apparatus of claim 1, further comprising a configuration that contains all or essentially all of the UV radiation from the radiation source from leaking out of the device when in use.

6. The apparatus of claim 1, further comprising a signaling component for signaling when the radiation source is emitting radiation and when it is not.

7. The apparatus of claim 1, wherein the ingress comprises an aperture through which the object can be put.

8. The apparatus of claim 1, wherein the ingress comprises a cradle into which the object can be placed, the cradle movably attached to the compartment and capable of moving into the compartment through the aperture.

9. The apparatus of claim 1, further comprising a spring loaded platform positioned proximal to the ingress and movable between positions, wherein the object to be sanitized can be placed through the ingress to push the platform to a position distal to the ingress into a locked, releasable position by a releasable latch which can release when a desired sanitizing cycle ends, wherein the object is enveloped by the compartment when the platform is pushed into the locked position.

10. The apparatus of claim 1, wherein a top portion of the compartment is attached to at least one side portion of the compartment by a hinging mechanism and is capable of covering the ingress, wherein the top portion is capable of being swung away from the compartment to allow the object to be positioned in the compartment and returning to its original position to envelop the object.

11. The apparatus of claim 1, further comprising electronic connectors for charging devices, connecting electronic devices, communication devices, internet devices, and combinations thereof.

12. The apparatus of claim 1, wherein the compartment is sized to accept cell phones and TV remotes, handheld devices, smart pads, keypads, jewelry, keys, credit cards, money, toiletry items, food related items, items that come into contact with food, food trays, dental and medical equipment and devices, writing utensils, kitchen utensils, books, magazines, gaming items, dice and playing cards, toys, balls, personal hygiene items, combs, brushes, toothbrushes, baby related objects, rubber nipples, containers, cordless telephone, smart phones, wireless headsets, portable media devices, digital cameras, video recorders, audio recorders, portable gaming devices, portable computing devices, tablet computers, laptop computers, notebook computers, electronic reading devices, personal digital assistants (PDA), palmtop computers, handheld computers, pen computers, ultra-mobile personal computers, pagers, portable navigation devices, personal navigation assistants, portable Global Positioning System units, personal electronic devices, personal hygiene devices, devices used by infants, portable data devices and other objects which can carry infectious organisms.

13. A method of sanitizing an object comprising the steps of:
   a. Providing an apparatus for sanitizing an object, comprising:
      i. a compartment comprising a top portion, a bottom portion and side portions and configured to envelop the object to be sanitized:
      ii. an ingress positioned in the compartment;
      iii. a component for reducing debris from the surface of the object to be sanitized; and
      iv. at least one radiation source within the compartment; wherein the at least one radiation source can provide UV radiation for deactivating infectious organisms;
   b. Positioning the object to be sanitized through the ingress into the compartment;
   c. Removing a portion of the debris from the surface of the object;
   d. Irradiating the object with radiation from the one or more radiation source; and
   e. Removing the object from the apparatus.

14. The method of claim 13, wherein the UV radiation is at least 253.7 nm.

15. The method of claim 13, wherein the component for reducing debris is at least one of a brush mechanism, an adhesive mechanism, an air impingement mechanism, a wiping mechanism or an electrostatic mechanism.

16. The method of claim 13, wherein the component for reducing debris is positioned proximal to the ingress.

17. The method of claim 13, wherein the apparatus further comprises a configuration that contains all or essentially all of the UV radiation from the radiation source from leaking out of the device.

18. The method of claim 13, wherein the apparatus further comprises a signaling component for signaling when the radiation source is emitting radiation and when it is not.

19. The method of claim 13, wherein the ingress comprises an aperture through which the object can be put.

20. The method of claim 19, wherein the ingress comprises a cradle into which the object can be placed, the cradle movably attached to the compartment and capable of moving into the compartment through the aperture.

21. The method of claim 13, further comprising a spring loaded platform positioned proximal to the ingress and movable between positions, wherein the object to be sanitized is placed through the ingress and pushes the platform to a position distal to the ingress into a locked, releasable position by a releasable latch which is released when a desired sanitizing cycle ends, wherein the object is enveloped by the compartment when the platform is pushed into the locked position.

22. The method of claim 13, wherein a top portion of the compartment is attached to at least one side portion of the compartment by a hinging mechanism and is capable of covering the ingress, wherein the top portion is capable of being swung away from the compartment to allow the object to be positioned in the compartment and returning to its original position to envelop the object.

23. The method of claim 13, further comprising electronic connectors for charging devices, connecting electronic devices, communication devices, internet devices, and combinations thereof.

24. The method of claim 13, wherein the compartment is sized to accept cell phones and TV remotes, handheld devices, smart pads, keypads, jewelry, keys, credit cards, money, toiletry items, food related items, items that come into contact with food, food trays, dental and medical equipment and devices, writing utensils, kitchen utensils, books, magazines, gaming items, dice and playing cards, toys, balls, personal hygiene items, combs, brushes, toothbrushes, baby related objects, rubber nipples, containers, cordless telephone, smart phones, wireless headsets, portable media devices, digital cameras, video recorders, audio recorders, portable gaming devices, portable computing devices, tablet computers, laptop computers, notebook computers, electronic reading devices, personal digital assistants (PDA), palmtop computers, handheld computers, pen computers, ultra-mobile personal computers, pagers, portable navigation devices, personal navigation assistants, portable Global Positioning System units, personal electronic devices, personal hygiene devices, devices used by infants, portable data devices and other objects which can carry infectious organisms.

* * * * *